(12) United States Patent
McCollum et al.

(10) Patent No.: US 8,073,711 B1
(45) Date of Patent: Dec. 6, 2011

(54) METHOD AND SYSTEM FOR OBTAINING HEALTH-RELATED RECORDS AND DOCUMENTS USING AN ONLINE LOCATION

(75) Inventors: Joe McCollum, Harpers Ferry, WV (US); Donna J. Briggs, Frederick, MD (US)

(73) Assignee: Healthport Technologies, LLC, Alpharetta, GA (US)

( * ) Notice: Subject to any disclaimer, the term of this patent is extended or adjusted under 35 U.S.C. 154(b) by 1990 days.

(21) Appl. No.: 09/589,647

(22) Filed: Jun. 7, 2000

(51) Int. Cl.
*G06F 19/00* (2011.01)

(52) U.S. Cl. .................................. 705/3; 705/2

(58) Field of Classification Search .................. 705/2, 3, 705/4, 40, 51, 64, 65, 1, 44, 67, 76, 50; 707/10, 707/104.1, 4, 102, 9; 455/3.04; 725/116; 345/810, 179; 235/379, 375, 462, 494; 358/403; 422/56, 58, 68.1; 713/165
See application file for complete search history.

(56) References Cited

U.S. PATENT DOCUMENTS

| | | | | |
|---|---|---|---|---|
| 5,321,520 | A * | 6/1994 | Inga et al. | 358/403 |
| 5,659,741 | A * | 8/1997 | Eberhardt | 707/104.1 |
| 5,737,539 | A * | 4/1998 | Edelson et al. | 705/3 |
| 5,754,939 | A * | 5/1998 | Herz et al. | 455/3.04 |
| 5,845,255 | A * | 12/1998 | Mayaud | 705/3 |
| 5,867,821 | A * | 2/1999 | Ballantyne et al. | 705/2 |
| 6,018,713 | A * | 1/2000 | Coli et al. | 705/2 |
| 6,032,120 | A * | 2/2000 | Rock et al. | 705/2 |
| 6,263,330 | B1 * | 7/2001 | Bessette | 707/4 |
| 6,463,417 | B1 * | 10/2002 | Schoenberg | 705/2 |
| 6,603,464 | B1 * | 8/2003 | Rabin | 345/179 |
| 6,725,200 | B1 * | 4/2004 | Rost | 705/3 |
| 6,874,085 | B1 * | 3/2005 | Koo et al. | 713/165 |
| 6,915,265 | B1 * | 7/2005 | Johnson | 705/2 |
| 6,988,075 | B1 * | 1/2006 | Hacker | 705/3 |
| 7,028,049 | B1 * | 4/2006 | Shelton | 707/104.1 |
| 2001/0037215 | A1 * | 11/2001 | Sparks | 705/2 |
| 2001/0041991 | A1 * | 11/2001 | Segal et al. | 705/3 |
| 2002/0083014 | A1 * | 6/2002 | Brickell et al. | 705/76 |

OTHER PUBLICATIONS

Anonymous. InstantDocuments.com Contracts Mynd Corporation As Reseller. May 25, 2000. Business Wire; New York. [Retrieved on Nov. 18, 2002]. Retrieved from ProQuest.*

Fischer, Karin. Rockefeller proposes Net privacy bill: Legislation would require user's OK to collect data. May 23, 2000. Charleston Daily Mail; Charleston. [Retrieved on Nov. 18, 2002]. Retrieved from ProQuest.*

* cited by examiner

*Primary Examiner* — Gerald J. O'Connor
*Assistant Examiner* — Natalie A Pass
(74) *Attorney, Agent, or Firm* — Lando & Anastasi, LLP (57) ABSTRACT

The invention described herein is directed to a method and system for obtaining health-related records and documents using an online location and is applicable in the business-to-business and business-to-customer business models. The present method and system also provides secure online ordering, tracking, storing, and exchanging health-related information between health-related entities. This is achieved by providing an electronic health information (EHI) web site on the Internet, allowing insurance personnel to order patients' records and documents from a central online location. In this manner, insurance companies will save time and realize significant cost savings while expediting the retrieval process of records and documents.

18 Claims, 11 Drawing Sheets

532 — Press 'Select Facility' to specify where the documents/records are currently located.

[A]

Select Facility

Melvins House of Fish
208 Main Street
Whitecastle, AS. 33221

You currently have no facility request associated with this order. Please select the facilities where the documents/records can be found.

Select all facilities before proceeding to Step 4

CANCEL—GO TO MAIN MENU

539

560

| | |
|---|---|
| ☐ Any and all records (does not include types marked in orange) | ☐ Consultation Reports |
| ☐ Admission Report | ☐ Pathology Reports |
| ☐ Discharge Report | ☐ Radiology/Nuclear Reports |
| ☐ ER Records | ☐ Delivery Records |
| ☐ Lab Reports | ☐ Newborn Notes |
| ☐ Operative Reports | ☐ X-Ray Films |
| ☐ All Physicians Notes | ☐ Nuclear Scans |
| ☐ All Nurses Notes | ☐ Physical Therapy Notes |
| ☐ Physicians Orders | ☐ Itemized Bills/CPT, Diagnostic Code, Writeoffs and Adjustments |

534 — [B] Select the types of records you are interested in at this facility. Types marked in orange will result in a separate facility request for that specific information.

536 — [C] Please select the dates of service for this facility request. If you have selected 'Any and All Records' in Section B, you don't need to fill this section out as you are requested ALL records for this patient regardless of dates of service. If you leave Starting Date and Ending Date blank, we'll request records that have any date of service.

Starting Date [ ]
Ending Date [ ]

538 — [D] Press 'Add' to add this facility request to your order. You will be taken back to the top of our screen.

ADD FACILITY TO MY ORDER

METHOD AND SYSTEM FOR OBTAINING HEALTH-RELATED RECORDS AND DOCUMENTS USING AN ONLINE LOCATION

FIELD OF THE INVENTION

The present invention relates to a method and system for providing health-related services to businesses and individuals. More particularly, the present invention is directed to a method and system for obtaining health-related records and documents using an online location. In addition, the present invention is directed to business-to-business and business-to-customer applications that provide secure online ordering, tracking, storing, and exchanging health-related information.

BACKGROUND OF THE INVENTION

As the Internet continues to grow in popularity and becomes an integral part of every day life, more and more people and businesses use it for various reasons. For example, businesses use the Internet to promote their products and services with hopes that consumers will use and purchase them. Thus, without question, many businesses believe that presence on the Internet is an important and necessary component for staying competitive in today's marketplace.

There are currently hundreds of businesses that advertise, promote, and sell health-related products/services through the Internet. As is well known, the health industry is a multi-billion dollar industry and it continues to grow exponentially. Part of the reason for such high cost associated with the health industry is the administration burdens placed on these health-related businesses.

For example, there are literally millions of records, forms, documents, etc., that are generated in this industry. For insurance personnel, the process of securing the millions of records and documents from health care providers, clinics, hospitals and other entities is a nightmare. Insurance personnel obtaining individual records and documents from multiple sources using postal mail, telephone, and fax are faced with long delays and errors in receipt of these time-sensitive records and documents. As a result, insurance personnel become easily frustrated and expend a considerable amount of time and money obtaining individual records and documents from health care providers.

In today's highly competitive marketplace, there is a great need for insurance companies and personnel to provide the most optimal service to their customers. In particular, there is a great need for a more efficient, reliable, and cost-saving method and system for obtaining health-related records and documents of patients. The inventors of the present invention believe that no comprehensive method and system exist today that allow insurance companies and personnel to obtain health-related records and documents of patients by using a single online web site on the Internet.

SUMMARY OF THE INVENTION

In view of the above-described problems of the prior art, it is an object of the present invention to provide a method and system for providing/obtaining health-related records and documents using an online location on the Internet.

It is another object of the present to provide a more efficient, reliable, and cost-saving method and system for obtaining health-related records and documents of patients.

It is still another object of the present invention to provide a business method for providing secure online ordering, tracking, storing, and exchanging health-related records and documents.

It is yet another object of the present invention to provide a method and system for requesting patients' records and documents via an electronic medium such as the Internet.

It is yet another object of the present invention to provide a highly efficient, effective, organized, and comprehensive system and method for obtaining health-related records and documents.

It is still another object of the present invention to provide Internet-based business-to-business and business-to-customer applications for obtaining health-related records and documents.

These and other objects of the present invention are achieved by providing an electronic health information (EHI) site on the Internet. The present invention allows insurance personnel to order patients' records and documents from a central online location (web site) or EHI site. The EHI then provides the insurance personnel an "authorization for release of records and documents" cover letter. The cover letter having an encoded barcode, along with a patient authorization letter, is submitted back to the EHI by the insurance personnel. After an EHI employee has approved the patient's authorization, the EHI then sends the two letters to a health provider, clinic, hospital, etc., requesting it to send the patient's records and documents to a pre-selected facility. The insurance personnel can then retrieve the records and documents from this facility.

In addition, the records and documents can be sent directly to the EHI location for scanning or imaging such that they can be transmitted to the insurance personnel via the Internet or by postal mail. The insurance company will save time and realize significant cost savings while expediting the retrieval process of records and documents.

BRIEF DESCRIPTION OF THE DRAWINGS

These and other objects and advantages of the present invention will become apparent and more readily appreciated from the following detailed description of the presently preferred exemplary embodiments of the invention taken in conjunction with the accompanying drawings, of which:

FIGS. 5A-5F illustrate user interface windows presented to the user in accordance with the preferred embodiment of the present invention.

DETAILED DESCRIPTION OF THE PREFERRED EMBODIMENTS

The present invention will now be described in greater detail, which will serve to further the understanding of the preferred embodiments of the present invention. As described elsewhere herein, various refinements and substitutions of the various embodiments are possible based on the principles and teachings herein.

The preferred embodiments of the present invention will now be described with reference to FIGS. 1-6, wherein like components, entities, services, applications, and steps are designated by like reference numerals throughout the various figures. Further, specific details and parameters are provided herein and are intended to be explanatory rather than limiting.

The present invention relates to a method and system for obtaining health-related records and documents using a central online location. In particular, the present invention allows insurance personnel to order patients' records and documents from the online location (web site) or electronic health information (EHI) site. In this manner, the insurance company will save time and realize significant cost savings while expediting the retrieval process of records and documents. Additionally, the present invention is directed to business-to-business and business-to-customer applications that provide businesses and customers access to health-related records and documents.

The presently preferred embodiment of the invention is implemented through an electronic medium such as the Internet. Although the present invention is applicable in countless environments such as government, legal, sports, automotive, entertainment, recreation, family, travel, electronics, food, and the like, it is particularly suited in the health industry where obtaining records and documents from various entities can be quite time-consuming and burdensome. Thus, the presently preferred embodiment will now be described with reference to the health industry.

Figure 1:
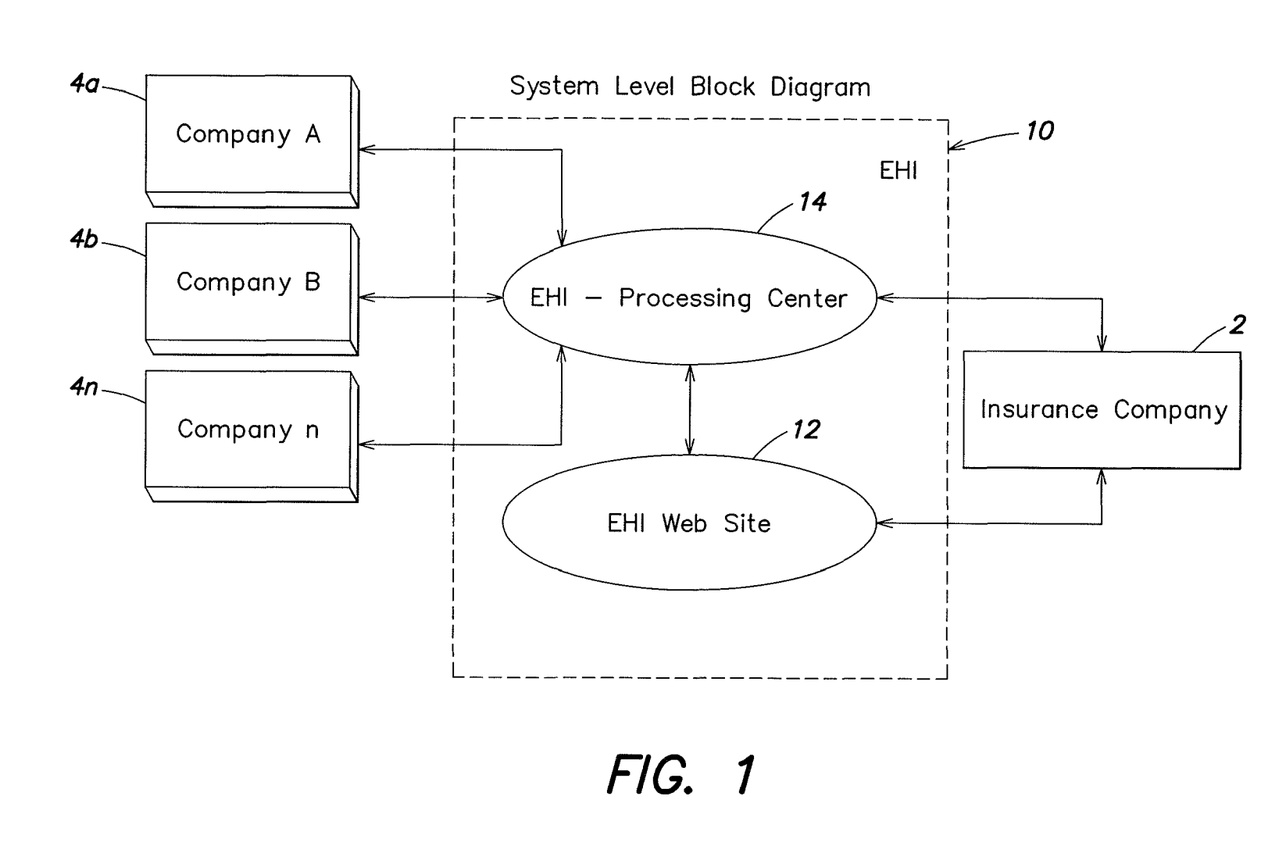
FIG. 1 illustrates a simplified system level block diagram in accordance with the preferred embodiment of the present invention.

FIG. 1 illustrates a simplified system level block diagram in accordance with the preferred embodiment of the present invention. The system includes an insurance company 2 communicating with an electronic health information ("EHI" hereinafter) entity 10. The EHI 10 further includes an EHI web site 12 and an EHI processing center 14, which are described in greater detail later herein. The insurance company 2 can access the EHI web site 12 using an URL (Universal Resource Locator) of the EHI 10. In addition to communicating with the insurance company 2, the EHI 10 further communicates with other entities such as company A 4a, company B 4b, company n 4n through the EHI processing center 14. The companies A—n 4a, 4b, 4n can be any entity having health-related records and documents of their customers/patients.

Figure 2:
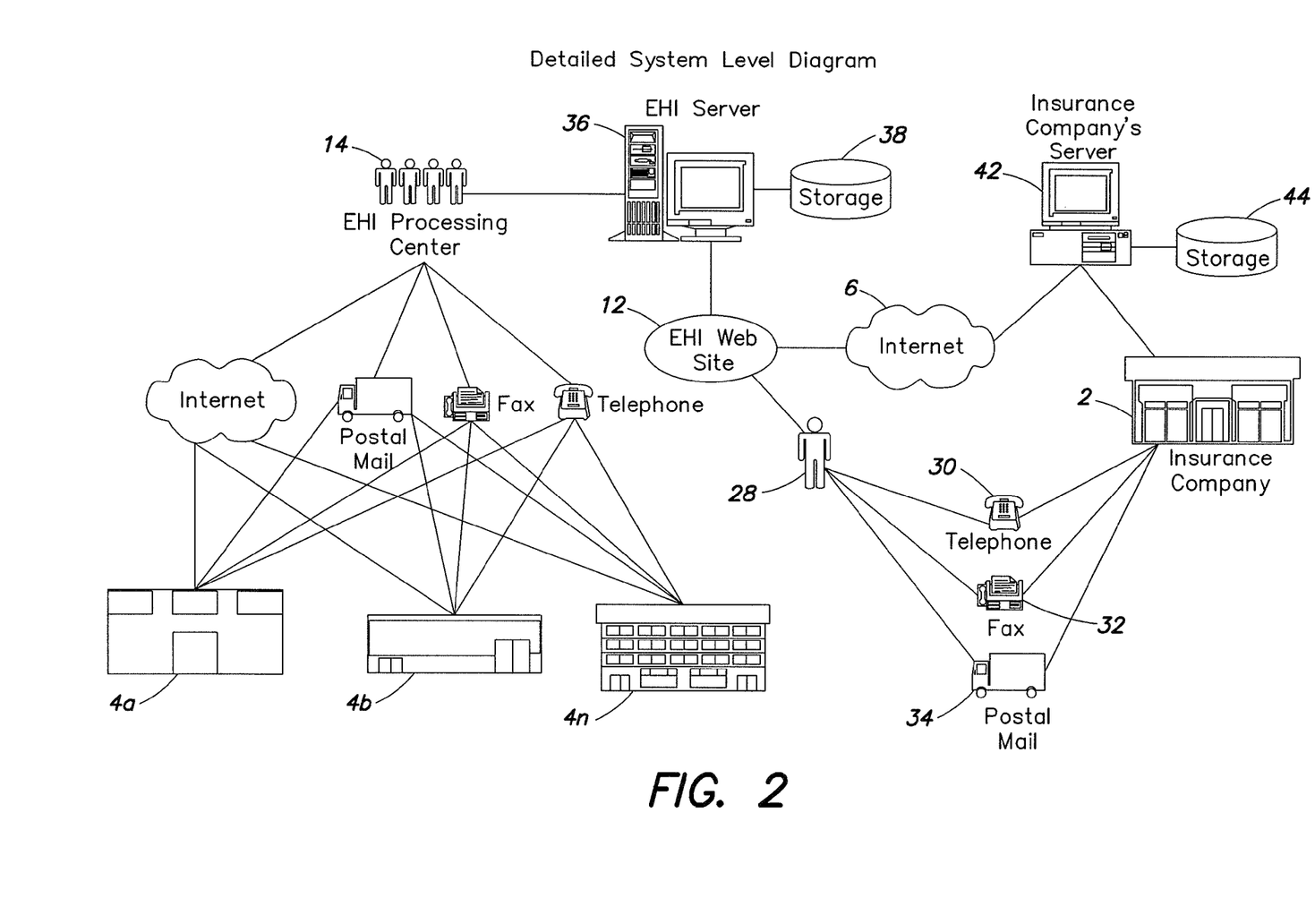
FIG. 2 illustrates a more detailed diagram of FIG. 1 in accordance with the preferred embodiment of the present invention.

FIG. 2 illustrates a more detailed diagram of FIG. 1 in accordance with the preferred embodiment of the present invention. It is noted that multiple insurance companies can be implemented in the preferred embodiment of the present invention, but only one insurance company is illustrated herein for ease of explanation and understanding.

In the preferred embodiment, the insurance company 2, using its server 42 or any other computing device, can access the Internet 6 using one of many commercially available browsers developed by companies such as Netscape (e.g., Navigator—believed to be a Registered Trademark of Netscape Corp.) or Microsoft (e.g., Internet Explorer—believed to be a Registered Trademark of Microsoft Corp.). Through the Internet 6, the insurance company 2 can access the EHI web site 12 for ordering, tracking, and managing patients' records and documents. As described above and in greater detail hereinafter, the EHI web site 12 is a well-organized comprehensive site that enables the insurance company 2 to obtain records and documents of individuals and other entities in an efficient and effective manner. The EHI site 12 is described in greater detail later herein When an employee (or using automated method) at the insurance company 2 logs on to the EHI site 12, the insurance company's server 42 is preferably be connected to an EHI server 36. The EHI web site 12 is preferably password protected giving access to insurance companies having the appropriate passwords and usernames. Once the insurance company 2 is connected (hardwired or wireless) to the EHI web site 12, the insurance company 2 can place orders for patients' record and documents. The EHI server 36 performs the function of processing retrieval orders received from the insurance company 2 for patients' records and documents.

In addition to using the server 42, the insurance company 2 can access the EHI site 12 using other computing devices such as a cellular phone (with Internet access capabilities), laptop computer, desktop computer, PDA (portable digital assistant), Net appliance, and the like. The computing device used by the insurance company 2 can be any device so long as it can transmit and receive data via the Internet 6. Alternatively, when there are electrical power outages and/or server problems, the insurance company 2 can access the EHI web site 12 indirectly by using a conventional telephone 30, fax 32, or postal mail service 34 to contact an on-site EHI employee 28. The EHI employee 28 can then access the EHI site 12 fulfilling any order from the insurance company 2.

The EHI web site 12 is associated with the EHI server (web and/or email) 36. As known, an email server is traditionally used to manage, send, and receive an email to/from the customer insurance company 2, while a web server is used to support and manage web sites. Further connected to the EHI server 36 is a data storage/database 38 to store and save insurance companies specific data, profiles, events, and the like.

The insurance company's server 42 can be functionally similar to the server 36 for managing, maintaining, storing, etc., its own data and applications. In addition, another data storage/database 44 can be connected to the server 42 for storing and saving data. Although shown externally to the servers 36, 42, the data storage/databases 38, 44 can be placed internally in the servers 36, 42.

The EHI processing center 14 processes the orders received from the insurance company 2. The processing center 14 contacts via telephone, mail, fax, Internet, etc, the companies A 4a, company B 4b, company n 4n for requesting the patients' records and documents.

Figure 3:
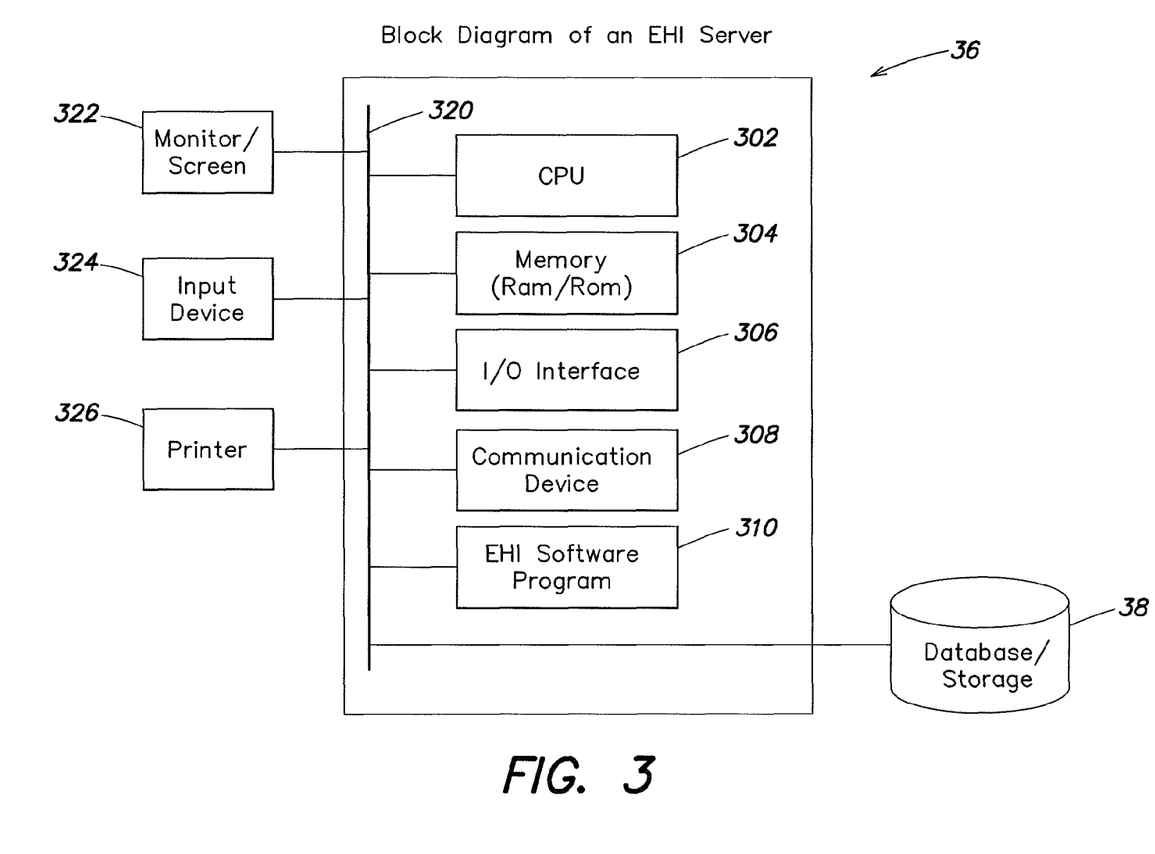
FIG. 3 illustrates a block diagram of a EHI server in accordance with the preferred embodiment of the present invention.

FIG. 3 illustrates a block diagram of an EHI server 36 in accordance with the preferred embodiment of the present invention. The EHI server 36, which is used to implement the present invention, typically includes a processor such as CPU 302, internal memory (RAM, ROM) 304 and I/O interface 306, which are coupled to a bus 320. The bus 320 may include multiple physical buses interconnected by bridges, adapters, controllers, and the like. Further coupled to the bus 320 is a communication device 308 for transmitting and receiving data via the Internet 6. The communication device 308 provides the EHI server 36 with connections to the Internet 6 and may be any device suitable for such purpose, such as a conventional modem, ISDN adapter, xDSL modem, cable modem, wireless, etc. The EHI server 36 may also include I/O devices such a monitor (screen) 322, input device (keyboard, pointing device, microphone) 324, and printer 326, which are also coupled to the bus 320.

In addition to the conventional components described above, an EHI software program 310 is included in the EHI server 36 for running applications and managing the data storage/database 38. The software program 310 can also include searching, sorting, and organizing capabilities for the data storage/database 38. The functional components described herein are preferably implemented through the EHI software program 310 that is processed by the CPU 302. Those of ordinary skill in the art will recognize other combinations of hardware and software components are readily applicable in the present invention, and that more than one software program 310 can be used herein.

As will be apparent to those skilled in the art, the EHI server 36 can run any of numerous operating systems, and the software program 310 can be implemented in any of numerous appropriate computer programming languages or combinations thereof, although, preferably, it is implemented, at least in part, in a language that is suitable for database access, manipulation and encoding (barcode).

The database 38 coupled to the bus 320 preferably includes a non-volatile storage medium such as CD-ROM, DVD, magneto-optical storage, external ROM, etc. The database 38 is used to store and save information pertaining to each insurance company and patient. Other components which are not illustrated herein, but which are commonly used in the EHI server 36, may also be included herein.

Figure 4:
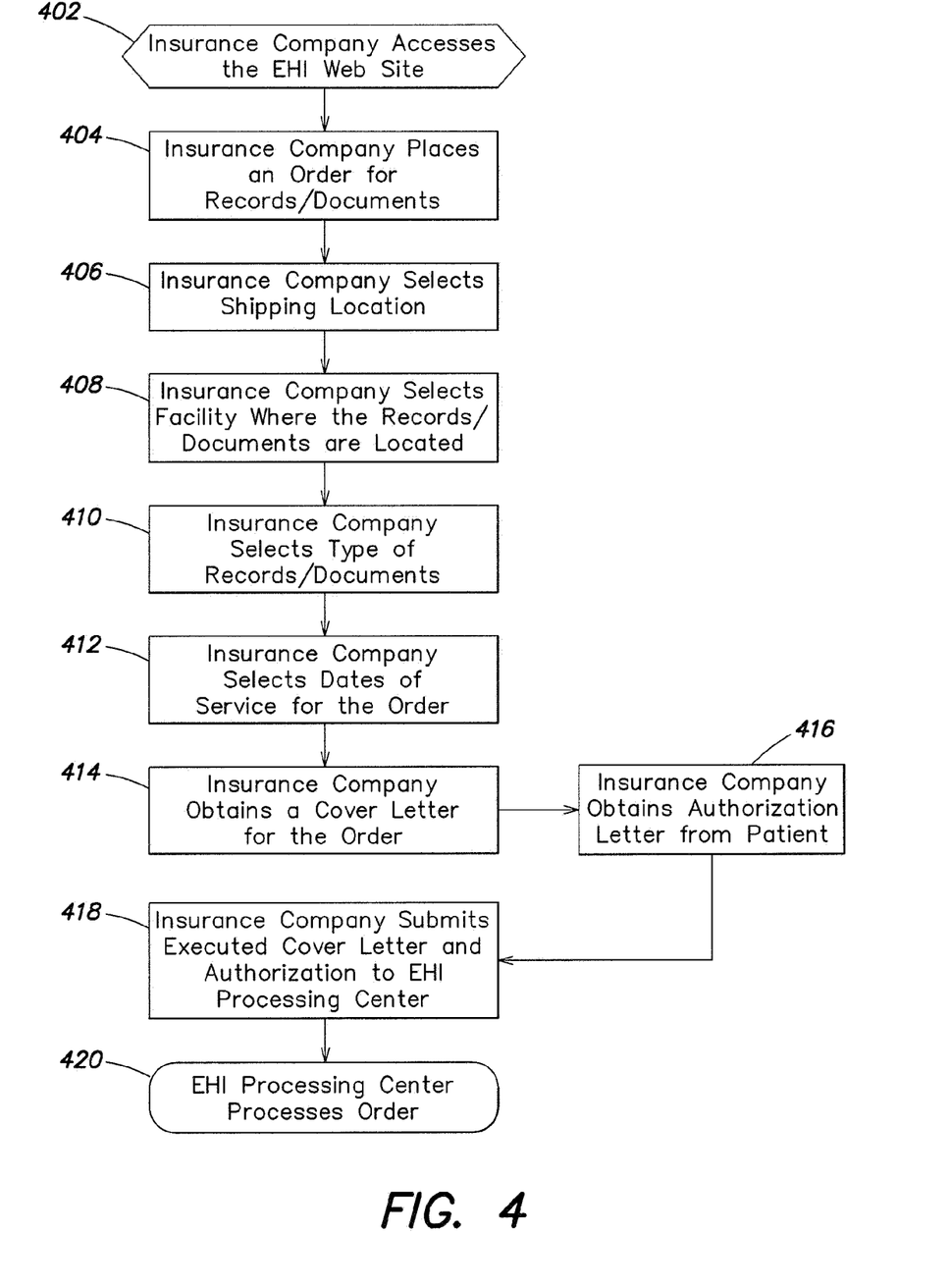
FIG. 4 illustrates a method for obtaining records and documents in accordance with the preferred embodiment of the present invention.
Figure 5A:
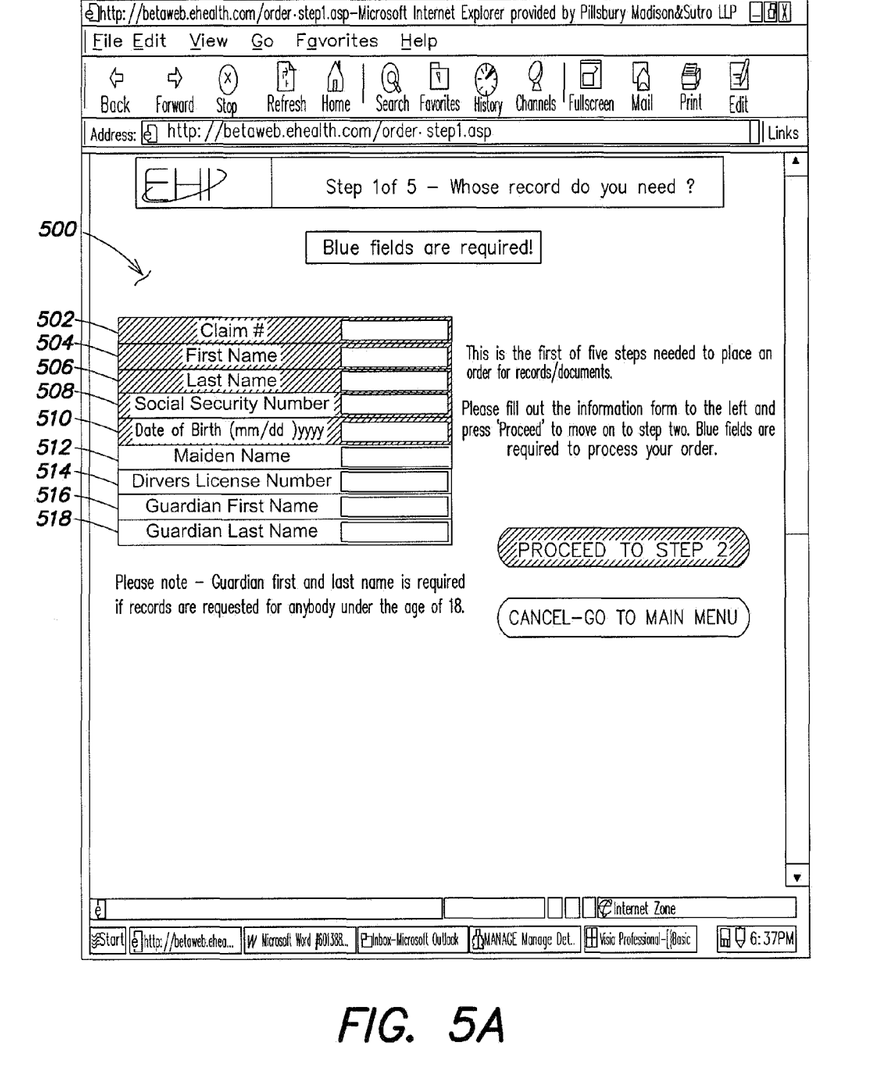

FIG. 4 illustrates a method for obtaining records and documents in accordance with the preferred embodiment of the present invention. In step 402, an employee such as a claims Examiner from the insurance company 2 ("IC employee" hereinafter) accesses the EHI web site 12 (i.e., EHI web server 36) via the Internet 6 using any of the methods described above. The IC employee begins the ordering process by inputting patient information in a graphical user interface window associated with the EHI web site 12 in step 404. FIG. 5A illustrates an example of the user interface window 500 for inputting patient's information. In this example, the required fields corresponding to the patient are the claim number 502, first name 504, last name 506, social security number 508, and date of birth 510. The IC employee may input other information such as maiden name 512, driver's ID number 514, and guardian first name 516 and last name 518, if required.

Figure 5B:
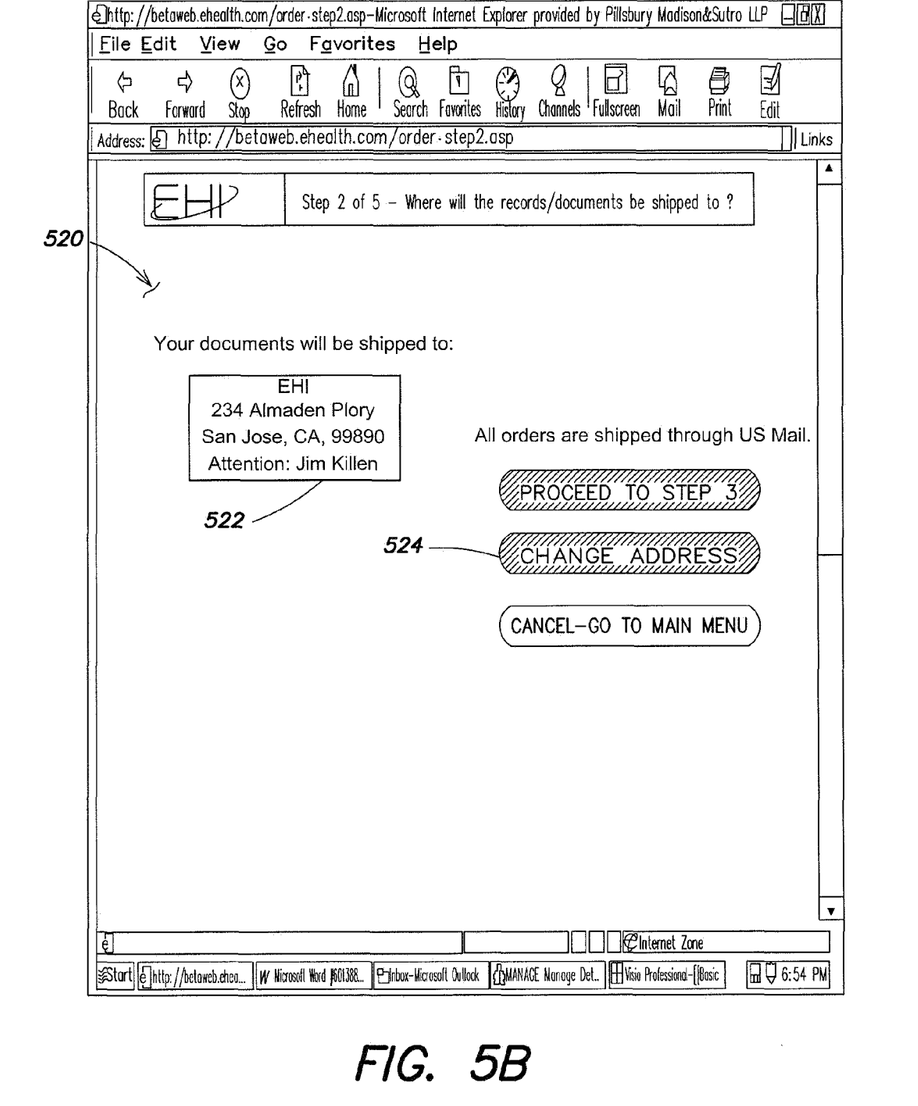

After inputting the patient information, the IC employee selects the shipping location of the records or documents in step 406. A user interface window 520 such as the one illustrated in FIG. 5B is displayed to the IC employee for selecting the shipping location. The IC employee can accept the default shipping location 522 or change the location using button 524.

Once the shipping location is selected, the IC employee next selects the facility where the records/documents are located, type of records/documents, and dates of service in steps 408, 410, and 412, respectively. The IC employee is presented with a user interface window such as window 530 in FIG. 5C for making these selections. In window 530, the IC employee selects (1) the facility location of the records/documents using section 532, (2) the type (section 539) of records/documents to be ordered in section 534, and (3) the dates of service in section 536. Section 538 can be used to add the currently selected facility for the current order.

Figure 5D:
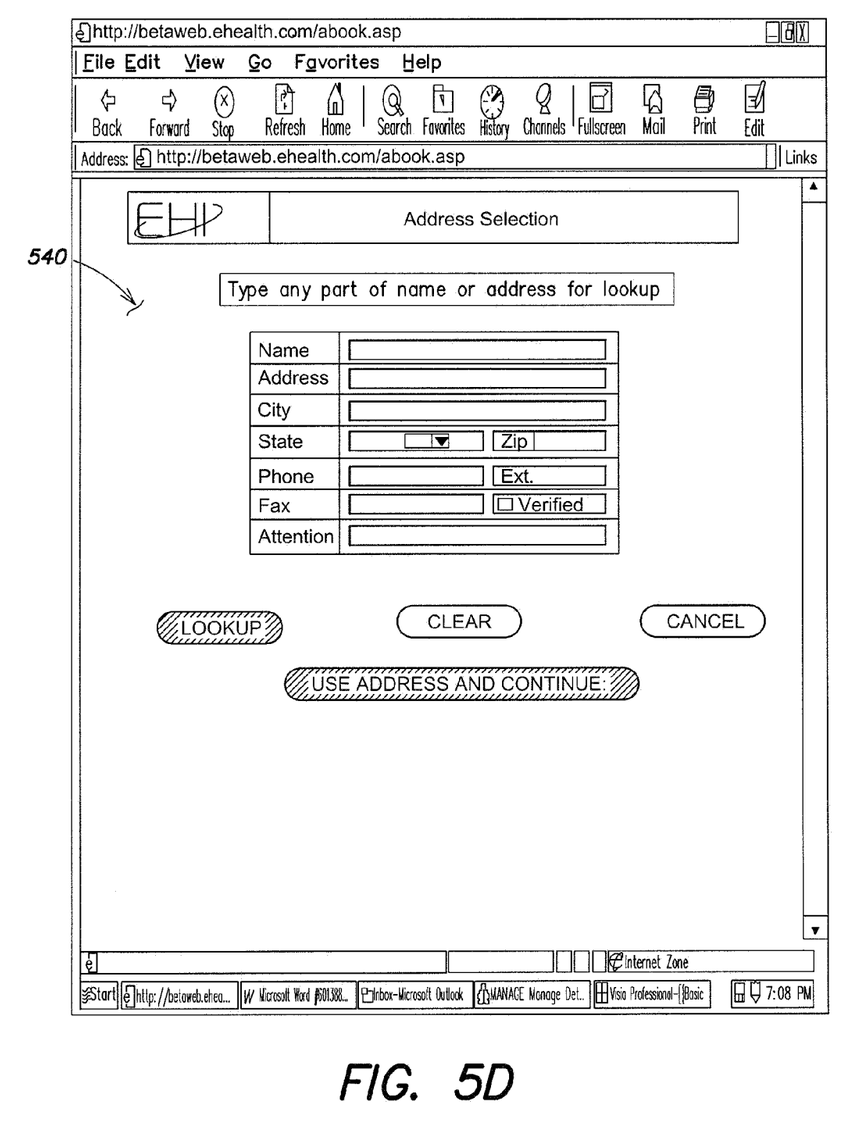
Figure 5E:
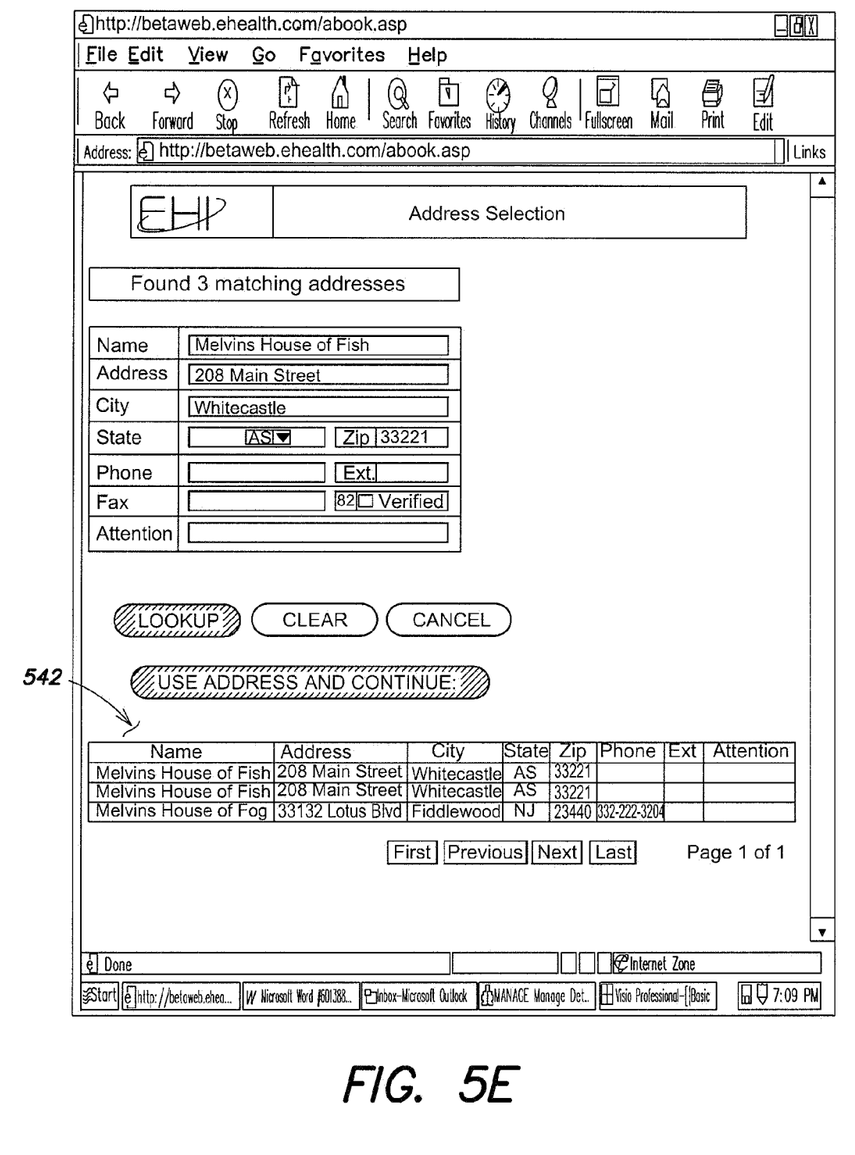

In greater detail, when the IC employee selects the "select facility" button in section 532, the IC employee is presented with a user interface window 540 as shown in FIG. 5D. The IC employee can use the window 540 to select the current location of the records/documents. When multiple locations are shown to contain the same records/documents, the IC employee is presented with a user interface window 542 as shown in FIG. 5E for selecting the appropriate facility. After selecting the appropriate facility in step 408, the IC employee is presented with a user interface window 550 as shown in FIG. 5F.

After making all the necessary selections, the insurance company is provided with an "authorization for release of records and documents" cover letter ("cover letter" hereinafter) in step 414. The cover letter can be downloaded from the EHI web site 12 during the session in PDF format or any other format acceptable to the insurance company 2. The EHI web site 12 establishes a unique identifier for each order.

Figure 6:
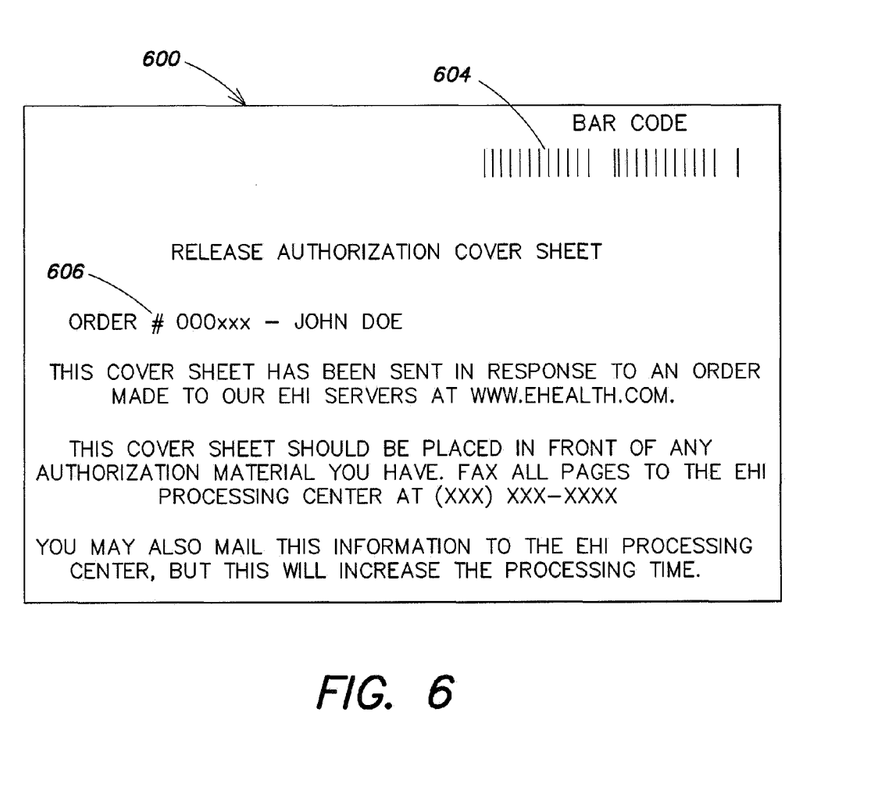
FIG. 6 illustrates a sample authorization cover sheet in accordance with the preferred embodiment of the present invention.

FIG. 6 illustrates an example of the cover letter 600 in accordance with the preferred embodiment of the present invention. The cover letter 600 includes an encoded barcode 604 and an order number section 606, which functions are describe in greater detail below.

The IC employee then prints out a hard copy of the cover letter 600 and obtains a second patient's authorization letter in step 416. The IC employee can then fax using the fax machine 32 or mail using postal mail 34 the cover letter 600 and the patient's authorization letter to the EHI processing center 14 in step 418.

If the cover letter 600 and/or the patient's authorization letter are not faxed/mailed in a timely manner, the EHI software program 310 or any other program running on the EHI server 36 automatically sends an e-mail to the insurance company 2 requesting the status of these letters. In addition, if these letters are not provided to the EHI processing center 14 in a certain period of time (e.g., 2 weeks), the order for the patient's records/documents is cancelled and an e-mail is sent to the insurance company 2 confirming such cancellation.

As discussed above, there are two methods of sending the cover letter 600 and the patient's authorization letter to the EHI processing center 14.

If the cover letter 600 and patient's authorization letter are faxed to EHI processing center 14, an automated program (e.g., fax machine or computing system having image and/or barcode reading capability) receives the call and stores the images by directing them to an input folder and providing them unique filenames. The automated program then locates the files and changes the format to Tiff files. The automated program (which is linked to the database 38) can also store the images in another location on the database, denoting them as being converted.

The automated program further reads the images and identifies the encoded barcode 604. After reading the barcode 604, the automated program writes the pertinent information to a database 38, along with the image file location. If, for some reason, the fax copy is illegible, the automated program generates an error log and indicates (e.g., with a green light or other symbol) that there is an error. In this case, an EHI employee can correct the problem by manually searching for the corresponding order. Thereafter, the images are manually sent to the automated program to be processed.

If, on the other hand, the cover letter 600 and patient's authorization letter are mailed to EHI processing center 14, the EHI employee manually opens the mail and scans it. The automated program will then move the image of the cover letter 600 and the patient's authorization letter to an individual file, again using the barcode 600 as identifiers. The automated program then writes the pertinent information to the database 38, along with the image file location.

Once the EHI processing center 14 receives the cover letter 600 and patient's authorization letter, the order is processed in step 420.

The EHI web site 12 can further be used to track and manage the records, documents, and orders. For example the EHI web site 12 changes the status of the order (which can be easily viewed by the IC employee) from "order entered" to "authorization received" status. The EHI employee, by using the EHI web site 12, can also view the cover letter 600 and the patient's authorization letter using the information in the database 38. If the patient's authorization is found to be authentic, the EHI employee approves the authorization by interacting with the EHI web site 12. The database 38 is then updated and the order status will change to "request approved." The same automated program that checks for the timeliness of receiving the cover letter 600 and patient's authorization letter also checks to determine when the authorization has been approved. Upon approval, the automated program sends a request for information letter to the printer for each facility the IC employee has selected. For each facility selected, a request letter along with a copy of the patient authorization's letter is sent to the facility.

In the case that the authorization is rejected, an e-mail is automatically sent to the IC employee with a brief description of why the authorization was rejected. Upon receipt of all the requested records, an EHI employee will put an entry into the EHI web site 12 stating that the records and documents have been received and the order status will be changed to "complete."

The presently preferred embodiment of the invention is implemented with the above-described processes. However, it is important to note that the present invention is applicable with any number of processes than those described hereinabove.

In the previous descriptions, numerous specific details and examples are set forth such as specific components, windows, steps, etc., to provide a thorough understanding of the present invention. However, as one having ordinary skill in the art would recognize, the present invention can be practiced without resorting to the details and examples specifically set forth.

Although various preferred embodiments have been described in detail above, those skilled in the art will readily appreciate that many modifications of the exemplary embodiment are possible without materially departing from the novel teachings and advantages of this invention.

We claim:

1. A method of obtaining a patient record containing information concerning an identified patient from a record custodian company through a record processing center computer in communication with the record custodian company, using a record ordering computer server, comprising:
   requesting an order, by a requestor, for the patient record concerning the identified patient from the record ordering computer server, including identifying the record processing center holding the patient record and a shipping location to which the patient record is to be delivered, by inputting patient information in a graphical user interface window presented by the record ordering computer server through a web site served by the record ordering computer server;
   providing to the requestor, by the record ordering computer server, a single cover letter having a machine readable, bar code identifier and human readable information, identifying the order requested;
   providing to the requestor, by the identified patient, a patient authorization letter authorizing release of the patient record concerning the identified patient;
   submitting from the requestor to the record processing center a submission including the cover letter along with the patient authorization letter, for completing the order;
   reading, using a computer of the record processing center, the machine readable, bar code identifier;
   in response to the machine readable, bar code identifier and the patient authorization letter, the record processing center computer automatically requesting the record custodian company in possession of the patient record concerning the identified patient to ship the patient record to the shipping location; and
   obtaining, by the requestor, the patient record concerning the identified patient from the shipping location.

2. The method according to claim 1, wherein the record ordering computer server comprises a web site.

3. The method according to claim 1, wherein the requestor comprises an insurance company.

4. The method according to claim 1 further comprising inputting patient information in a graphical user interface window before requesting the order.

5. The method according to claim 4, wherein the patient information includes at least one of a claim number, first name, last name, social security number, and date of birth.

6. The method according to claim 1, wherein sending the cover letter comprises faxing the cover letter to the processing center.

7. The method according to claim 6 further comprising automatically reading and identifying, by the processing center, the machine readable, bar code identifier on the cover letter.

8. The method of claim 1, wherein said cover letter is a paper letter.

9. The method of claim 8, wherein said patient authorization letter is a paper letter.

10. A system for obtaining a patient record containing information concerning an identified patient using a computer server connected to an electronic medium, comprising:
    a client software module stored in a computer memory of a computer operated by a requestor and by which the requestor requests from the computer server an order for the patient record concerning the identified patient, by inputting patient information in a graphical user interface window presented by the computer server through a web site served by the computer server;
    a software module stored in a computer memory of the computer server which provides to the requestor a single cover letter having a machine readable, bar code identifier and human readable information, identifying the order requested from the computer server;
    a communications system through which the requestor submits the cover letter along with a patient authorization letter, obtained by the requestor from the identified patient, authorizing release of the patient record, to a processing center; and
    a computer based database system operable automatically in response to the submission from the requestor of the cover letter and the patient authorization letter by the processing center, to request shipping the patient record concerning the identified patient to the shipping location.

11. The system according claim 10, wherein the requestor comprises an insurance company.

12. The system according to claim 10, wherein sending the cover letter comprises faxing the cover letter to the processing center.

13. The system according to claim 10, wherein sending the cover letter comprises mailing the cover letter to the processing center.

14. The system of claim 10, wherein said cover letter is a paper letter.

15. The system of claim 14, wherein said patient authorization letter is a paper letter.

16. A method of obtaining a patient record containing information concerning an identified patient from a record processing center using an electronic information web site associated with an electronic information server computer system, comprising:

accessing the electronic information web site by the requestor using an accessing computer client;

selecting by the requestor via the accessed electronic information web site the patient record concerning the identified patient, a record custodian holding the patient record and a shipping location to which the patient record is to be delivered, which together form an order;

downloading by the requestor from the accessed electronic information web a cover letter having a machine readable, bar code identifier and human readable information identifying the order;

storing the order selected by the requestor via the accessed electronic information web site in the electronic information server computer system;

providing to the requestor, by the identified patient, a patient authorization letter authorizing release of the patient record concerning the identified patient;

submitting from the requestor to the electronic information server computer system an electronic file containing the cover letter along with the patient authorization letter;

identifying the order in the electronic information server computer system using a software process executable on the electronic information server computer system reading the machine readable, bar code identifier the cover letter;

transmitting a request by the electronic information server computer system to the record custodian to ship the patient record to the shipping location; and     receiving by the requestor the patient record at the shipping location.

17. The method according to claim 16, wherein submitting comprises faxing the cover letter along with the patient authorization letter to a fax receiving terminal in electronic communication with the electronic information server computer system.

18. The method according to claim 16, wherein submitting comprises mailing the cover letter along with the patient authorization letter to the record processing center where they are scanned into the electronic information server computer system.

\* \* \* \* \*